United States Patent [19]

Plummer

[11] Patent Number: 4,943,726
[45] Date of Patent: Jul. 24, 1990

[54] TOMOGRAPHIC AND WHOLE BODY IMAGING TABLE

[75] Inventor: Steven J. Plummer, Hudson, Ohio

[73] Assignee: Picker International, Inc., Highland Heights, Ohio

[21] Appl. No.: 246,774

[22] Filed: Sep. 20, 1988

[51] Int. Cl.⁵ ............................................. G01T 1/166
[52] U.S. Cl. ........................... 250/363.02; 250/363.03; 250/363.04; 250/363.05
[58] Field of Search ...................... 250/363.02, 363.04, 250/363.05, 363.08; 378/209; D24/3; 269/322, 328

[56] References Cited

U.S. PATENT DOCUMENTS

| | | | |
|---|---|---|---|
| D. 246,880 | 1/1978 | Miola | D24/3 |
| 4,417,143 | 11/1983 | Haas et al. | 250/363.05 |
| 4,426,578 | 1/1984 | Bradcovich et al. | 250/363.08 |
| 4,649,277 | 3/1987 | Terra | 250/363.05 |

OTHER PUBLICATIONS

Technicare, Rectangular Field Camera Omega 500, 1981, all pages.

Primary Examiner—Constantine Hannaher
Assistant Examiner—Edward J. Glick
Attorney, Agent, or Firm—Fay, Sharpe, Beall, Fagan, Minnich & McKee

[57] ABSTRACT

A patient couch assembly (B) supports a patient such that a nuclear camera system (A) can scan the patient in either (i) a longitudinal mode or (ii) a transverse tomographic mode. A table top (20) is connected adjacent one corner with an undercarriage (30) that supports the table top above the floor. Generally vertical supporting portion (34) is connected only adjacent an intersection of a first side and a foot end (22) of the top (26). This enables a camera head (10) of the nuclear camera to move peripherally around a transverse central slice of the patient and the associated support position of the table top or to move longitudinally completely along the underside of the patient and table top from head to foot.

11 Claims, 2 Drawing Sheets

TOMOGRAPHIC AND WHOLE BODY IMAGING TABLE

BACKGROUND OF THE INVENTION

The present invention relates to structures for supporting patients and other subjects to facilitate examination. It finds particular application in conjunction with patient tables for nuclear cameras in which application it permits both transverse tomographic scanning and longitudinal whole body scanning. However, it will be appreciated that the present support will find utility in other applications where radiation treatment, radiation receiving, and other equipment is positioned both under and over the patient along a plurality of axes or planes.

Heretofore, nuclear cameras have been commonly utilized to perform transverse tomographic scans and whole body scans. In the tomographic scans, the camera head is rotated around the periphery of a slice or slice-like segment through the patient which is to be imaged. In a whole body scan, the camera is moved longitudinally along the upper or lower surface of the patient. Commonly, two patient support tables are provided with the x-ray scanner, one for tomographic transverse scans and another for whole body imaging.

Typically, the table tops are constructed of an expensive carbon fiber material. Hence, the inclusion of a second table is relatively expensive. Moreover, a closeby storage area is required for the table which is not in use.

Commonly, each prior art table had a lower base portion that extended under the table top. In the transverse tomographic table, the foot end of the table top was connected with a base or stand and the head end and central portion were cantilevered outward. The base or stand commonly had a member extending along the flow parallel to the top for greater stability. This table enabled ready motion of the camera head around a transverse slice of the patient's torso or around the patient's head. However, movement along the complete length of the patient was blocked by the base or stand. The whole body scanning table top was cantilevered from one longitudinal side. This permitted the camera head to move along the underside of the patient but interfered with transverse rotational movement.

To limit the storage space required, others have proposed a single base with two table tops. One table top attached to the base by the foot portion to facilitate transverse tomographic scanning. The other table top included the appropriate mounts for connecting a longitudinal side of the top to the base to facilitate whole body scanning. The second table top required less storage area but still involved the high cost of two carbon fiber table tops.

In accordance with the present invention, a single table design is provided which facilitates both transverse tomographic scanning and longitudinal whole body scanning.

SUMMARY OF THE INVENTION

In accordance with the present invention, a double cantilevered patient table is provided. A subject supporting top is supported by a support structure or undercarriage which permits a camera head or other equipment to be moved (1) longitudinally under the top and (2) transversely around an end or center portion of the top.

In accordance with a more limited aspect of the invention, the table undercarriage includes a vertical portion which is connected only adjacent one end of a longitudinal side of the top and a floor engaging portion which extends from the vertical portion generally under the top.

In accordance with a yet more limited aspect of the invention, the floor engaging portion includes at least three casters disposed generally adjacent and below front and back ends and longitudinal sides of the top.

In accordance with another aspect of the present invention, a scanning nuclear camera apparatus is provided. A camera head converts radiation from a subject into output signals indicative thereof. A double cantilevered patient table is provided for supporting the patient. A gantry means supports and moves the camera head (1) longitudinally around the table top and (2) transversely around an end portion of the top.

One advantage of the present invention is that it enables both tomographic and whole body scanning to be performed with a single table.

Another advantage of the present invention resides in reduced cost.

Still further advantages will become apparent upon reading and understanding of the following detailed description.

BRIEF DESCRIPTION OF THE DRAWINGS

The present invention may be embodied in various components and arrangements of components or in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
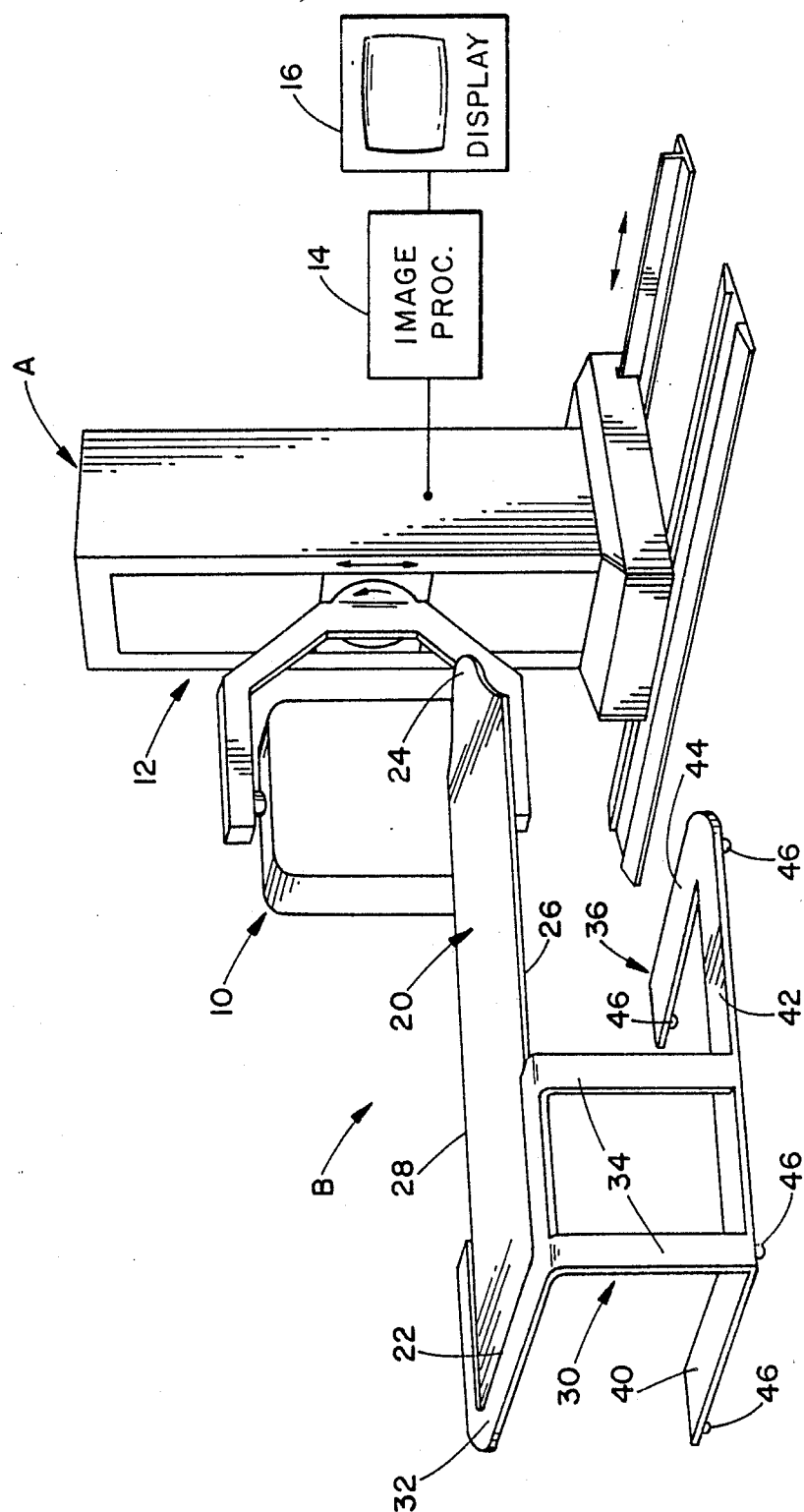
FIG. 1 is a perspective view of a nuclear camera system in accordance with the present invention: and, FIG. 2 is an alternate embodiment of the patient table; and, FIG. 3 is yet another alternative embodiment.

With reference to FIG. 1, a patient is examined by a nuclear camera system A while being supported on a patient or subject support table B. The nuclear camera system A includes a camera head 10 which receives radiation emanating from the patient and produces output signals indicative thereof. As is conventional in the art, the camera head includes a scintillation crystal which provides light flashes or scintillations in response to incident radiation. An array of photomultiplier tubes detects each scintillation event. The photomultiplier tubes are connected with position determining circuitry to ascertain the location of each scintillation, its energy, and other characteristics and produce the output signal which is indicative thereof.

A gantry means 12 supports the camera head 10 and moves it along a plurality of axes. More specific to the preferred embodiment, the gantry rotates the camera head about one horizontal axis and moves it longitudinally about a pair of orthogonal axes -- one vertical and one horizontal. Other gantry arrangements may be provided to move the camera in a transverse tomographic mode and a linear scan mode. In the transverse tomographic mode, the camera head moves circumferentially around a transverse slice of the patient with the camera head continuing to point perpendicular to the center of rotation. In a longitudinal scanning mode, the gantry moves the camera head longitudinally along the patient top or bottom side as may be appropriate to the selected medical procedure. The camera head normally remains parallel to the plane of the scan.

Image processing and reconstruction circuitry 14 processes the output signals of the camera head as it is moved during an examination into an image representation. The image representation may be displayed on a video monitor 16, stored in computer memory, stored on tape or disk for later recall, further processed, or the like.

The patient table B is a double cantilevered table arrangement. A subject supporting top 20 is elongated and contoured to accommodate a subject such as a human patient. In the illustrated embodiment, the top has a first or foot end 22, a second or head end 24, and first and second longitudinal sides 26, 28. The length of the patient table between the foot and head ends and its width between longitudinal sides are selected to accommodate a human patient. Preferably, the width of the table is minimal such that it does not interfere with the camera head during transverse tomographic scanning even of the slimmest patients. In the preferred embodiment, the top is constructed of a carbon fiber reinforced plastic resin, although other materials that pass radiation may also be utilized.

An undercarriage or support portion 30 supports the top 20 such that the camera head is free to move (1) longitudinally along the top and bottom surfaces of the top from beyond the first end to beyond the second end and (2) transversely around an end or central portion of the top. More specifically to the preferred embodiment, the carriage includes a U-shaped top retaining portion 32 which engages the foot end 22 of the top in a secure supporting relationship. A vertical supporting portion 34 extends from adjacent an intersection of the first end and first side of the top to a floor engaging portion 36. More specifically, the vertical supporting portion 34 extends between one side arm of the U-shaped retaining portion 32 and the floor engaging portion 36. The vertical supporting portion is disposed adjacent only one end of the top, the foot end in the illustrated embodiment, such that the head end is open and unencumbered for the camera head to rotate thereabout. Moreover, the vertical support portion is disposed adjacent one side edge of the top such that the camera head may move longitudinally along the upper or lower side of the top freely and without engaging the support structure.

Figure 2:
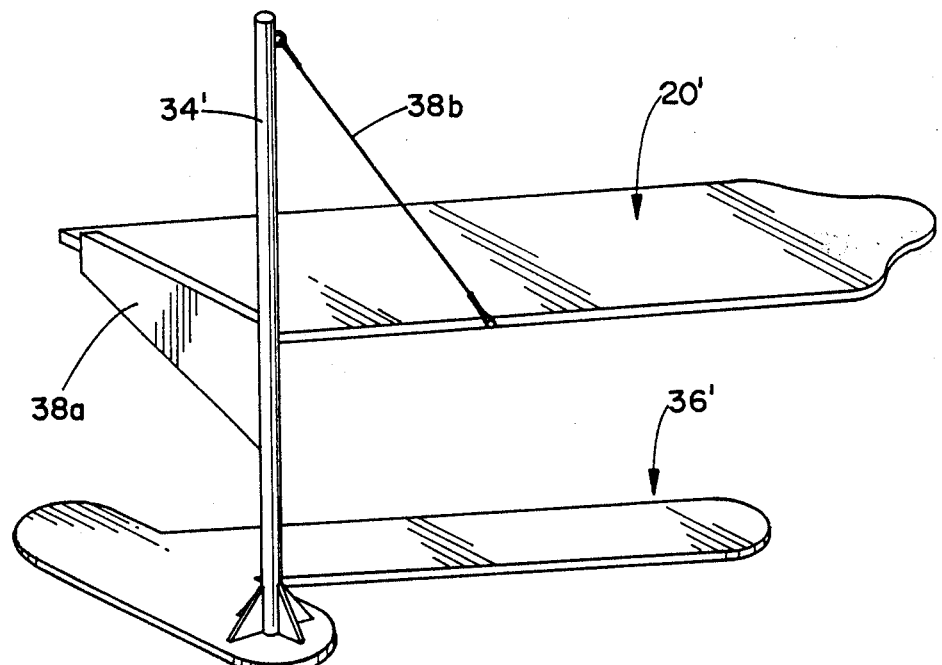
Figure 3:
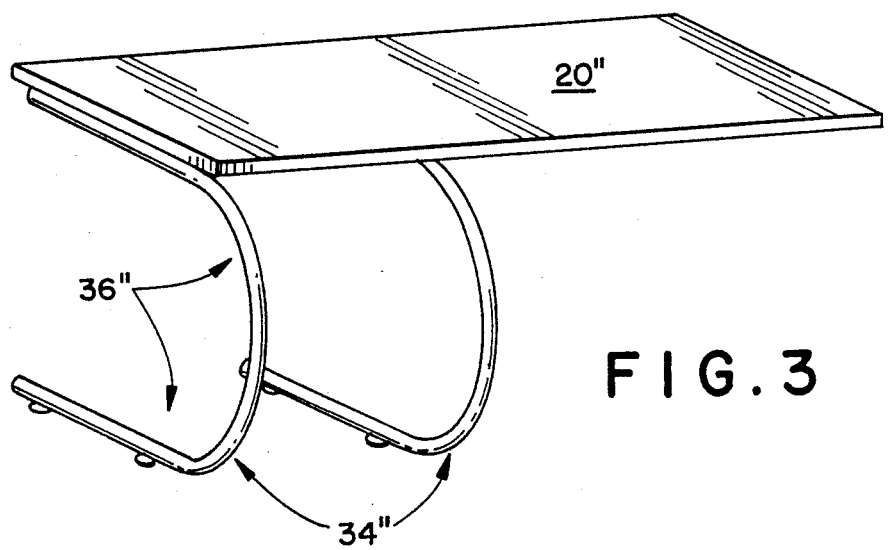

In the illustrated embodiment, the vertical supporting portion 34 is shown as a plurality of generally vertical members. It is to be appreciated, however, that other structures which hold the foot end of the top securely without interfering with the camera head in either mode may be utilized. With reference to FIG. 2, a single pole 34' might extend vertically between a corner of the top 20 and the floor engaging portion 36'. A first cantilevering structure 38a holds the top stably cantilevered along a side to side axis and second cantilevering means 38b supports the top cantilevered along an end to end axis. With reference to FIG. 3, the vertical supporting portion 34' may extend at an angle or along a curved path. Optionally, the vertical portion may include hydraulic, pneumatic, or mechanical lifts to adjust the height of the table.

With reference again to FIG. 1, the floor engaging portion 36 includes a first leg 40 which extends generally the width of the top and a second leg portion 42 which extends longitudinally a sufficient percentage of the length of the top that it is stable when supporting a human patient. To improve stability, another leg portion 44 extends from one of the first and second leg portions. A plurality of casters 46, such as lockable rollers to permit the table to be moved or held stationary, are mounted to the under side of the floor engaging portion. To optimize stability while still providing ready access to the table top, casters are positioned adjacent either side of the top and adjacent either end. More specific to the illustrated embodiment, casters are disposed adjacent the corners defined by the sides and bottom end and another pair of casters are disposed under the sides generally adjacent the top end of the table top. Although four or more casters or points of contact with the floor may improve stability, adequate stability may be had with as few as three casters or points of contact. Of course, if the floor engaging portion 36 rests completely and directly on the floor without casters, its lower most continuous surface provides a continuous array of casters or points of contact with the floor.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A scanning nuclear camera apparatus comprising:
   a camera head for converting radiation from a subject into output signals indicative thereof;
   a subject supporting top having a head end, a foot end, and first and second sides;
   a gantry means for supporting and selectively moving the camera head (1) longitudinally along upper and lower surfaces of the top, and (2) peripherally around a central portion and the head end of the top; and,
   an undercarriage for supporting the top without interfering with the movement of the camera head and without interfering with reception by the camera head of radiation events emanating from the supported subject during the peripheral movement of the camera head, the undercarriage including:
   a top retaining portion disposed only adjacent the foot end of the top such that the head end and the central portion are free of the top retaining portion such that the top retaining portion is not juxtaposed between the support subject and the camera head as the camera head moves peripherally around the central portion and the head end of the top,
   a support portion extending from the top retaining portion adjacent an intersection of the first side and the foot end of the top to a floor engaging portion such that the head end and the second side are cantilevered from the support portion to provide free access for the camera head to move without interference from the support portion during both the longitudinal movement along the top lower surface and the peripheral movement around the central portion; and,
   an image means for constructing an image representation from the output signals.

2. The apparatus as set forth in claim 1 further including at least three casters mounted on a lower side of the floor engaging portion for engaging the floor, the casters being disposed generally below the front end, back end, and each side of the top.

3. The apparatus as set forth in claim 1 wherein the undercarriage includes:
   at least three floor engaging casters, the casters being disposed generally below each side of the top and toward the head end and the foot end.

4. The apparatus as set forth in claim 3 wherein the support portion includes a generally vertical member extending from the top first side to a floor frame portion, the floor frame portion being connected with the casters.

5. The apparatus as set forth in claim 1 wherein the top retaining portion is generally U-shaped, extends around the foot end of the top, and receives the top therein, the generally U-shaped portion extending along the first and second sides less than halfway to the head end.

6. A double cantilevered patient table comprising:
   a subject supporting top having first and second ends and first and second sides extending between the first and second ends; and,
   an undercarriage which supports the top in a generally horizontal plane, yet provides access for a camera head to be moved (1) longitudinally under and over the entire length of the top, and (2) peripherally around the top and the first and second sides adjacent a generally central portion, the undercarriage including:
      a floor engaging portion that engages the floor at at least three points adjacent the ends and the sides of the top,
      a generally U-shaped top retaining portion which extends around the first end of the top and receives the top therein,
      a generally vertical member connected with a side of the generally U-shaped retaining portion and with the floor engaging portion.

7. The table as set forth in claim 6 wherein the generally vertical member is connected adjacent an intersection of the first side portion of the top and the first end portion of the top such that the second end and the second side of the top are cantilevered from the generally vertical member to provide free access of the camera thereadjacent.

8. The table as set forth in claim 6 further including at least three casters mounted on a lower side of the floor engaging portion for engaging the floor, the casters being disposed generally below at least three of the first end, the second end, and the first side and the second side of the top.

9. The table as set forth in claim 7 wherein the undercarriage includes at least three floor engaging casters, the casters being disposed generally below the first and second sides of the top and toward the first and second ends; and,
   a plurality of members connecting the casters with the generally vertical member.

10. A method of scanning a patient with a nuclear camera, the method comprising:
    supporting the patient on a radiation transmissive table top which is supported by an undercarriage connected generally at one corner thereof;
    moving a head of the nuclear camera below the table top from beyond a first end longitudinally to beyond a second end;
    without moving the patient, circumferentially rotating the camera head completely around a central transverse section of the patient and a corresponding portion of the table top;
    such that the patient is scanned longitudinally from the first end to the second end peripherally around the transverse section without moving the patient, without the undercarriage interfering with movement of the camera head, and without the undercarriage interfering with receipt of radiation from the patient by the camera head.

11. A patient table for use with a nuclear camera that performs both transverse tomographic scans and longitudinal, whole body scans, the patient table comprising:
    a patient supporting top having a head end, a foot end, and first and second sides;
    a top retaining portion disposed only adjacent a foot end of the top such that the head end is free of the top retaining portions;
    a support portion extending from the top retaining portion adjacent an intersection of the foot end and a first side of the top such that the head end and a second side of the top are cantilevered from the support portion;
    a floor engaging portion connected with the support portion to support the support portion, hence the top retaining portion and top stably on the floor.

* * * * *